United States Patent
Yevmenenko et al.

(10) Patent No.: US 11,278,664 B2
(45) Date of Patent: Mar. 22, 2022

(54) INFUSION ADAPTER

(71) Applicant: Becton Dickinson and Company Limited, Dun Laoghaire (IE)

(72) Inventors: Yan Yevmenenko, New York, NY (US); Andrew Wong, East Hanover, NJ (US); Brent Huber, Saratoga Springs, UT (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 874 days.

(21) Appl. No.: 14/991,226

(22) Filed: Jan. 8, 2016

(65) Prior Publication Data
US 2016/0199569 A1     Jul. 14, 2016

Related U.S. Application Data

(60) Provisional application No. 62/101,551, filed on Jan. 9, 2015.

(51) Int. Cl.
*A61M 5/14*     (2006.01)
*A61M 5/162*     (2006.01)
(Continued)

(52) U.S. Cl.
CPC .......... *A61M 5/1413* (2013.01); *A61J 1/1481* (2015.05); *A61J 1/201* (2015.05);
(Continued)

(58) Field of Classification Search
CPC .. A61M 5/1413; A61M 5/1412; A61M 5/162; A61M 5/1782; A61M 39/10;
(Continued)

(56) References Cited

U.S. PATENT DOCUMENTS 4,515,283 A * 5/1985 Suzuki ................ A61M 1/0001
                                                215/270
4,629,159 A * 12/1986 Wellenstam .......... A61M 39/26
                                               137/614.18
(Continued)

FOREIGN PATENT DOCUMENTS

| EP | 0728490 A2 | 8/1996 |
|---|---|---|
| JP | 51106385 A | 9/1976 |

(Continued)

*Primary Examiner* — Scott J Medway
*Assistant Examiner* — John A Doubrava
(74) *Attorney, Agent, or Firm* — The Webb Law Firm

(57) ABSTRACT

An infusion adapter for connection with an infusion fluid container includes a connection portion configured to engage an injection port of an infusion fluid container, and a port configured to connect to an intravenous line, with the port in fluid communication with the connection portion. The connection portion includes a retaining ring extending radially outward from the connection portion, with the retaining ring configured to securely connect the infusion adapter to the infusion fluid container to substantially prevent disconnection of the infusion adapter from the infusion fluid container once the infusion adapter is connected to the infusion fluid container. The retaining ring includes an indicator configured to provide visualization of insertion of the connection portion into an injection port of an infusion fluid container.

10 Claims, 14 Drawing Sheets

(51) Int. Cl.
*A61M 5/178* (2006.01)
*A61J 1/20* (2006.01)
*A61M 39/10* (2006.01)
*A61J 1/14* (2006.01)

(52) U.S. Cl.
CPC ........... *A61J 1/2058* (2015.05); *A61J 1/2075* (2015.05); *A61M 5/1412* (2013.01); *A61M 5/162* (2013.01); *A61M 5/1782* (2013.01); *A61M 39/10* (2013.01); *A61M 39/1011* (2013.01); *A61J 2200/70* (2013.01); *A61M 2039/1044* (2013.01); *A61M 2039/1072* (2013.01); *A61M 2039/1077* (2013.01)

(58) Field of Classification Search
CPC .... A61M 39/1011; A61J 1/1481; A61J 1/201; A61J 1/2058; A61J 1/2075; A61J 2200/70; A61J 2039/1044; A61J 2039/1072; A61J 2039/1077
See application file for complete search history.

(56) References Cited

U.S. PATENT DOCUMENTS

| 4,695,276 | A | * | 9/1987 | Shinno | A61M 25/0014 604/533 |
|---|---|---|---|---|---|
| 5,211,638 | A | | 5/1993 | Dudar et al. | |
| 5,368,177 | A | * | 11/1994 | Derksen | A61J 1/1406 215/247 |
| 5,520,420 | A | * | 5/1996 | Moretti | F16L 37/00 285/81 |
| 5,569,222 | A | * | 10/1996 | Haselhorst | A61M 39/10 604/533 |
| 2003/0191445 | A1 | * | 10/2003 | Wallen | A61M 5/1408 604/411 |
| 2005/0245867 | A1 | * | 11/2005 | Olsen | A61M 25/00 604/118 |
| 2005/0245899 | A1 | | 11/2005 | Swisher | |
| 2006/0200093 | A1 | | 9/2006 | Lopez | |
| 2008/0262475 | A1 | * | 10/2008 | Preinitz | A61M 39/10 604/533 |
| 2009/0204080 | A1 | * | 8/2009 | Balteau | A61M 5/162 604/249 |
| 2011/0049866 | A1 | | 3/2011 | Trombley, III et al. | |
| 2014/0150911 | A1 | | 6/2014 | Hanner et al. | |

FOREIGN PATENT DOCUMENTS

| JP | 62119946 U | 7/1987 |
|---|---|---|
| JP | 9131405 A | 5/1997 |
| JP | 10290842 A | 11/1998 |
| JP | 200211097 A | 1/2002 |
| JP | 2003534877 A | 11/2003 |
| JP | 2003339821 A | 12/2003 |
| JP | 2005169113 A | 6/2005 |
| JP | 2005522281 A | 7/2005 |
| JP | 2009233286 A | 10/2009 |
| JP | 201063866 A | 3/2010 |
| WO | 9119462 | 12/1991 |
| WO | 2004052430 A2 | 6/2004 |
| WO | 2011014525 A2 | 2/2011 |
| WO | 2014033706 A2 | 3/2014 |

\* cited by examiner

INFUSION ADAPTER

CROSS-REFERENCE TO RELATED APPLICATION

This application claims priority to U.S. Provisional Application Ser. No. 62/101,551, filed Jan. 9, 2015, which is hereby incorporated by reference in its entirety.

BACKGROUND OF THE INVENTION

1. Field of the Disclosure

The present disclosure relates generally to an infusion adapter and, more particularly, to an infusion adapter for securely connecting the adapter to an intravenous bag for a drug transfer procedure.

2. Description of the Related Art

Intravenous therapy applications allow patients to receive infusion and medication treatment. For example, therapy may include the administration of medications by IV using intravenous and subcutaneous or hypodermis routes, i.e., into the bloodstream and under the skin. Examples of medical treatments that intravenous therapy applications may provide to a patient include antibiotics, pain management medications, cancer treatments, and similar medications.

Medications may be packaged as "pre-filled" devices, wherein a syringe assembly is pre-filled with medication prior to being packaged and delivered to a patient. "Pre-filled" devices eliminate the need for a user to fill the device prior to injection.

Certain drugs or medications are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. In addition, drugs may be provided as multipart systems that require mixing prior to administration. For example, one or more liquid components, such as flowable slurries, and one or more dry components, such as powdered or granular components, may be provided in separate containers that require mixing prior to administration.

A patient may be provided with an intravenous system that includes intravenous tubing and a connector that is adapted to receive an injector and/or syringe assembly containing a required medication. In this manner, when a treatment is needed, a patient or a medical practitioner is able to connect a syringe assembly to the connector and then inject a medication intravenously into the patient via the injector and/or syringe assembly, the connector, and the intravenous tubing.

When performing infusion, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question. However, it has been found that an unsecure connection between the syringe and the injection port of the infusion bag may cause problems such as accidental or inadvertent disconnection of the syringe from the infusion bag, pollution of the working environment because of leakage, and high forces required to pierce a fluid barrier of the injection port of the infusion bag.

SUMMARY OF THE INVENTION

In one aspect, an infusion adapter for connection with an infusion fluid container includes a connection portion configured to engage an injection port of an infusion fluid container, and a port configured to connect to an intravenous line, with the port in fluid communication with the connection portion. The connection portion includes a retaining ring extending radially outward from the connection portion, with the retaining ring configured to securely connect the infusion adapter to the infusion fluid container to substantially prevent disconnection of the infusion adapter from the infusion fluid container once the infusion adapter is connected to the infusion fluid container. The retaining ring includes an indicator configured to provide visualization of insertion of the connection portion into an injection port of an infusion fluid container.

The indicator may be formed from a first material and a remaining portion of the retaining ring may be formed from a second material, with the first material being softer than the second material. The first material may be an elastomeric material, such as a thermoplastic elastomer.

The indicator may extend further radially outward than a remaining portion of the retaining ring. The retaining ring may include a first side and a second side positioned opposite the first side, where the indicator is annular and positioned between the first side and the second side of the retaining ring. The indicator may include a rounded outer portion.

The retaining ring may be positioned adjacent to a stop defined by a main body of the infusion adapter. The retaining ring may have a first side with a tapered, rounded surface and a second side positioned opposite the first side, with the second side of the retaining ring defining a sharp edge that is configured to engage a portion of the infusion fluid container upon an attempt to withdraw the infusion adapter from the infusion fluid container.

The infusion adapter may include a plurality of retaining rings. The connection portion may include a puncturing point. Further, the infusion adapter may include a syringe adapter port configured to connect with a syringe adapter. The retaining ring may be crenelated. The indicator may be formed via a two-shot molding process.

In a further aspect, an infusion adapter for connection with an infusion fluid container includes a connection portion configured to engage an injection port of the infusion fluid container, and a port configured to connect with an intravenous line, with the port in fluid communication with the connection portion. The connection portion includes a retaining ring extending radially outward from the connection portion, with the retaining ring is configured to securely connect the infusion adapter to the infusion fluid container to substantially prevent disconnection of the infusion adapter from the infusion fluid container once the infusion adapter is connected to the infusion fluid container. The retaining ring defines a plurality of teeth.

The teeth may be defined and spaced apart from each other via recesses. The plurality of teeth and the recesses may each be rectangular in shape. The retaining ring may include a first end and a second end positioned opposite the first end, with the recesses extending from the second end to a position intermediate the first end and the second end.

The retaining ring may be positioned adjacent to a stop defined by a main body of the infusion adapter. The retaining ring may have a first side with a tapered, rounded surface and a second side positioned opposite the first side, with the second side of the retaining ring defining a sharp edge that is configured to engage a portion of the infusion fluid container upon an attempt to withdraw the infusion adapter from the infusion fluid container.

The connection portion may include a puncturing point and the infusion adapter may further include a syringe adapter port configured to connect with a syringe adapter. The retaining ring may include an indicator configured to provide visualization of insertion of the connection portion into an injection port of an infusion fluid container.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
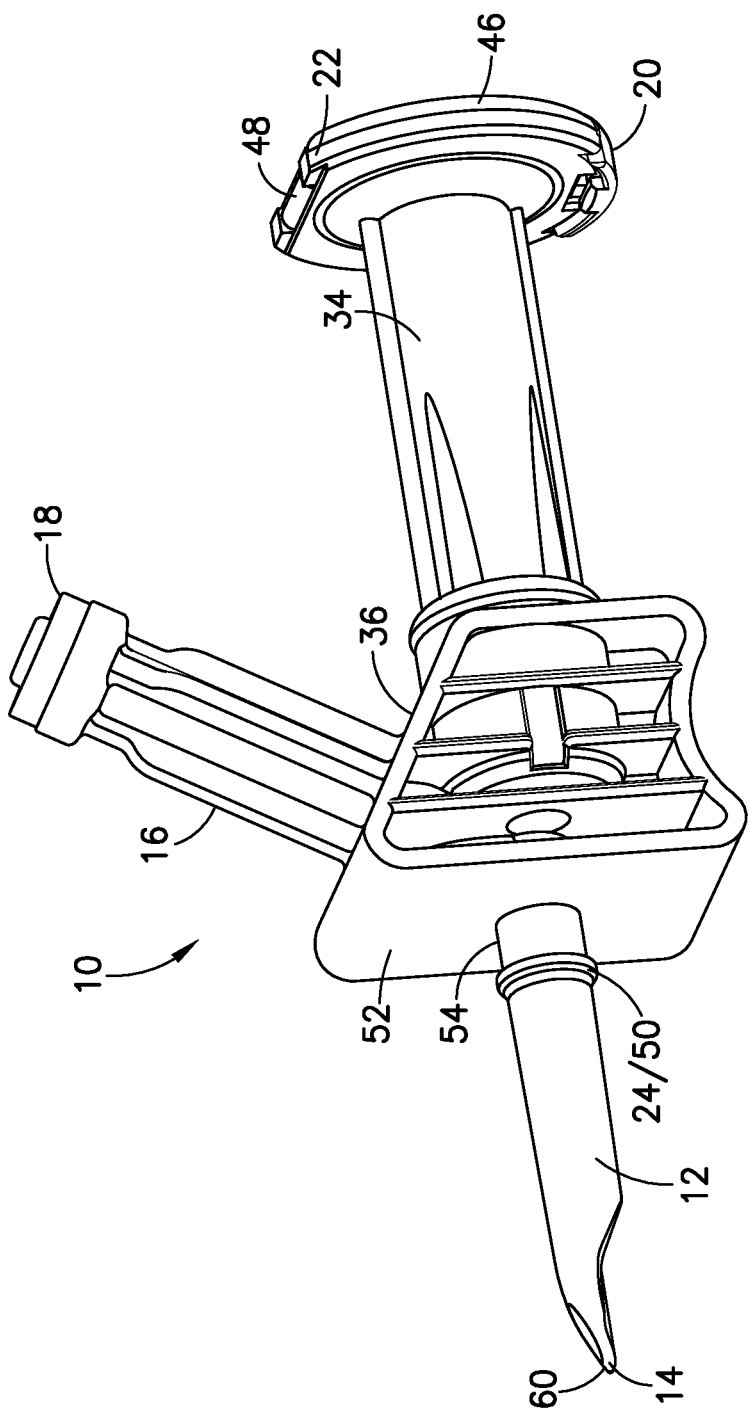
FIG. 1 is a perspective view of an infusion adapter according to one aspect of the present invention.
Figure 2:
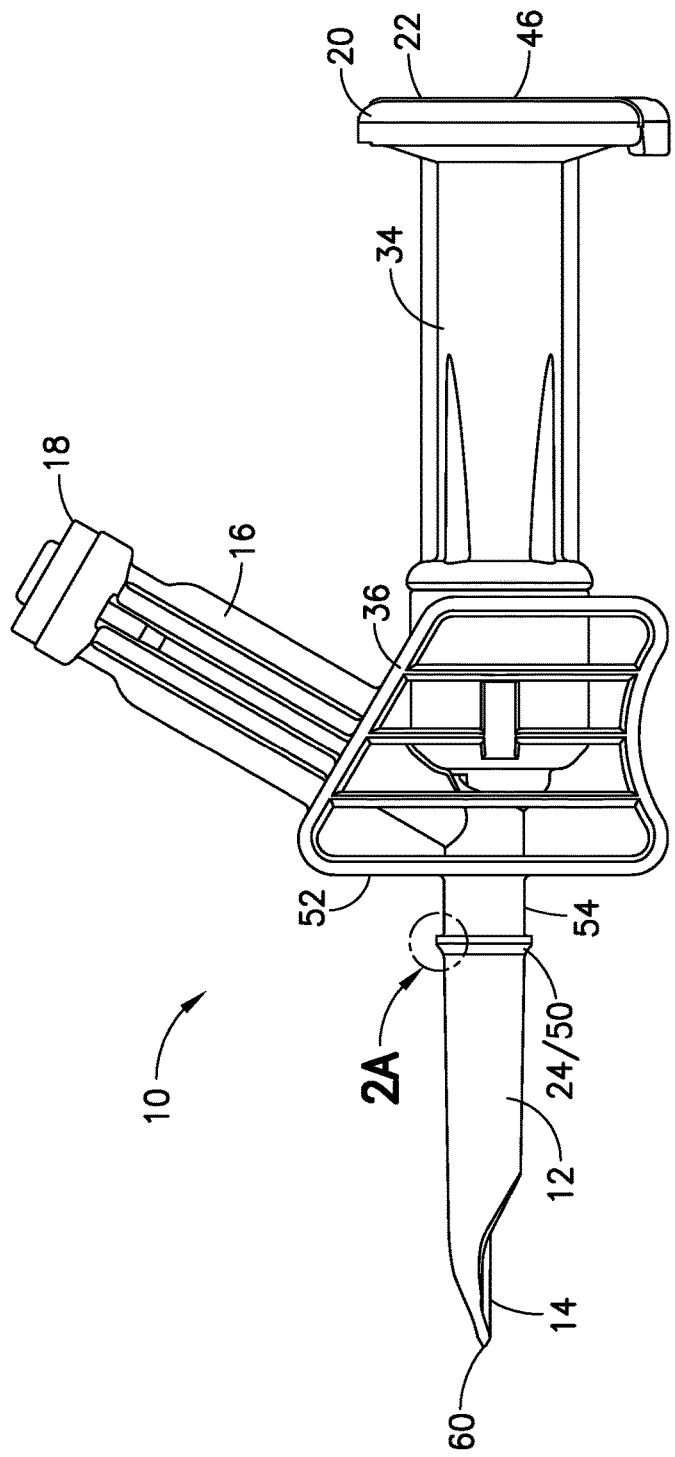
FIG. 2 is a right side view of the infusion adapter of FIG. 1 according to one aspect of the present invention.
Figure 2A:
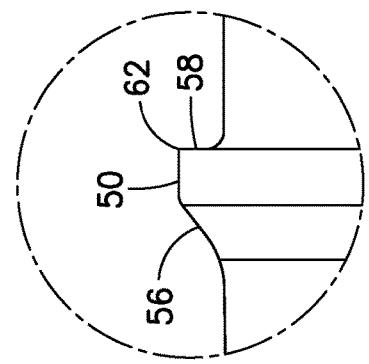
FIG. 2A is an enlarged view of area "2A" shown in FIG. 2 according to one aspect of the present invention.
Figure 3:
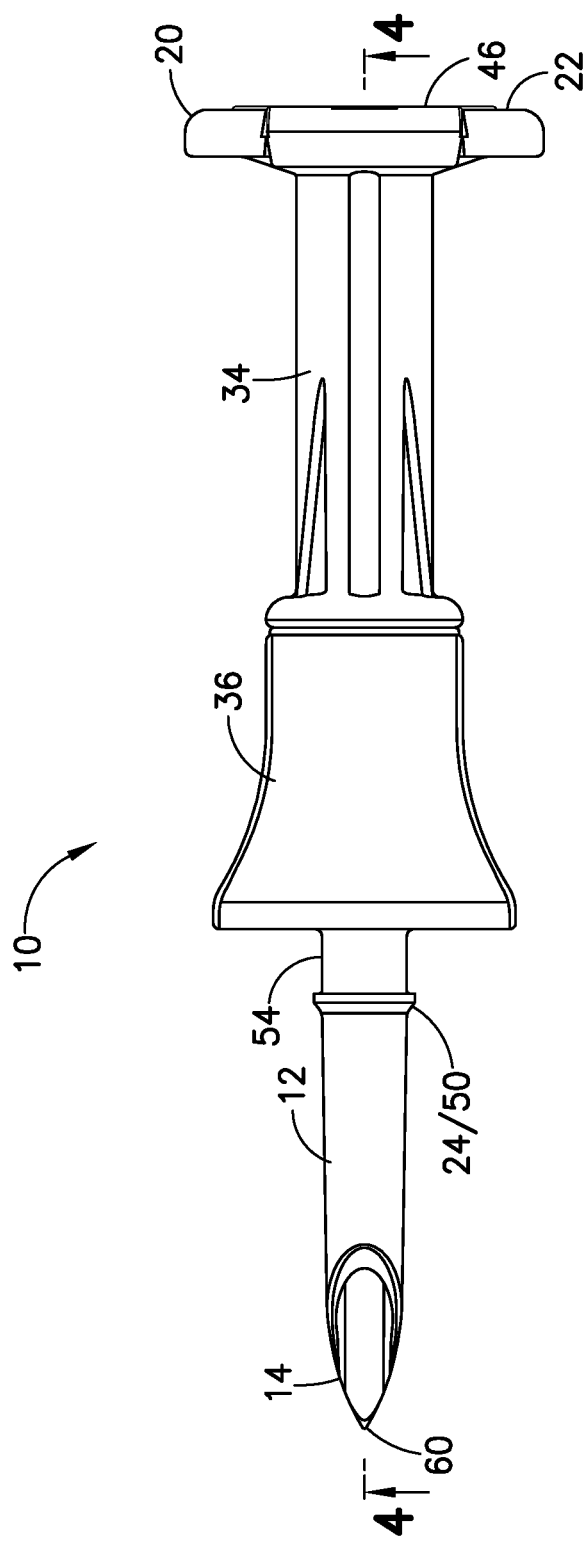
FIG. 3 is a bottom view of the infusion adapter of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-7, an infusion adapter 10 includes a connection portion 12 located at a first end 14, a first port 16 located at a first port end 18, and a second port 20 located at a second port end 22. Connection portion 12 includes an anchor component 24 and a fluid channel 26 and a fluid channel 32, although only a single channel arrangement may also be utilized. First port 16 includes a first port fluid channel 28 and second port 20 includes a second port fluid channel 30. As shown more clearly in FIGS. 4 and 7, the fluid channel 32 of connection portion 12 is in fluid communication with first port fluid channel 28 of first port 16 such that a fluid may flow into infusion adapter 10 at first port 16, travel through first port fluid channel 28 to fluid channel 32 of connection portion 12 and out first end 14 of infusion adapter 10. The fluid channel 26 of connection portion 12 is in fluid communication with second port fluid channel 30 of second port 20 such that a fluid may flow into infusion adapter 10 at first end 14 of connection portion 12, travel through fluid channel 26 to second port fluid channel 30 and out second port 20 of infusion adapter 10.

Referring to FIGS. 1-7, in one embodiment, infusion adapter 10 may comprise a generally Y-shape. Further, it is contemplated that infusion adapter 10 may be made available in a variety of shapes and sizes as long as first port 16 is spaced a distance from second port 20 so that first port 16 may be connected to a syringe assembly containing a medication fluid and second port 20 may be connected to an intravenous line that is adapted for connection to a bloodstream of a patient as will be described in more detail below. For example, in another embodiment, infusion adapter 10 may comprise a generally T-shape.

Figure 4:
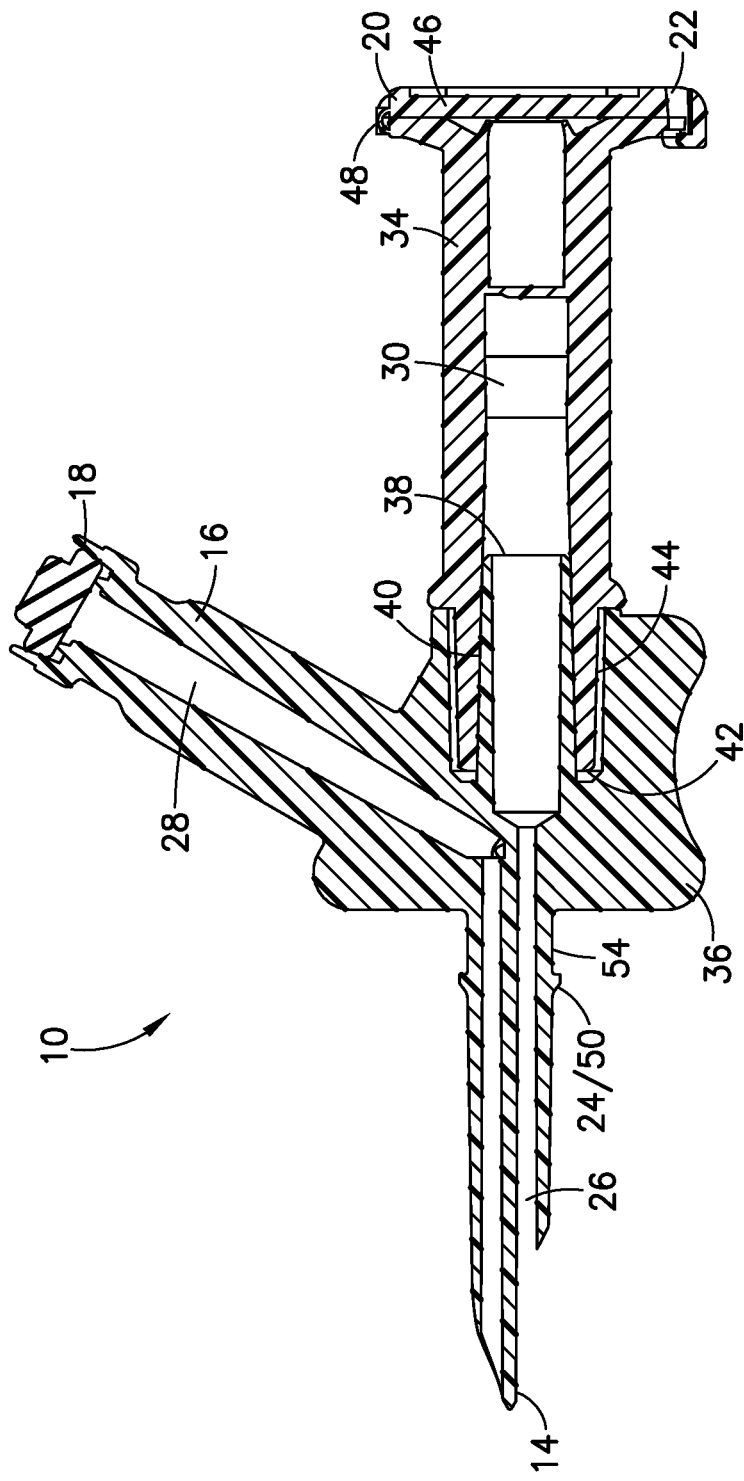
FIG. 4 is a cross-sectional view along line 4-4 shown in FIG. 3 according to one aspect of the present invention.
Figure 6:
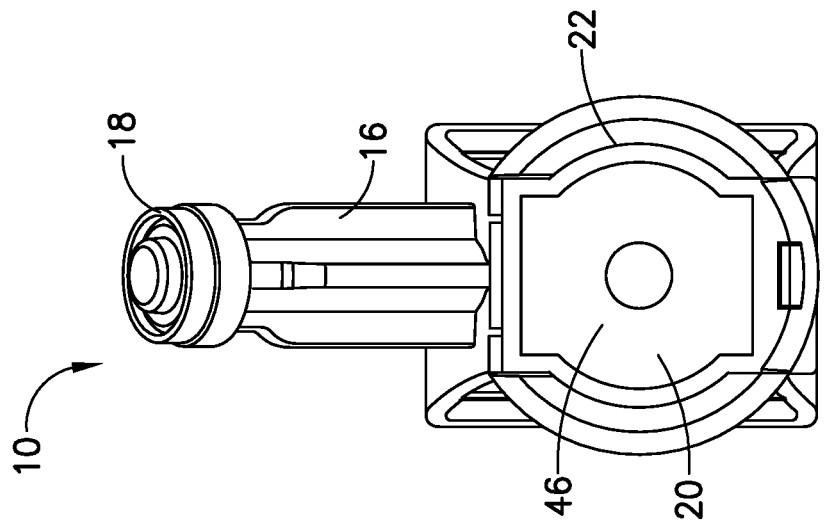
FIG. 6 is a rear view of the infusion adapter of FIG. 1 according to one aspect of the present invention.
Figure 5:
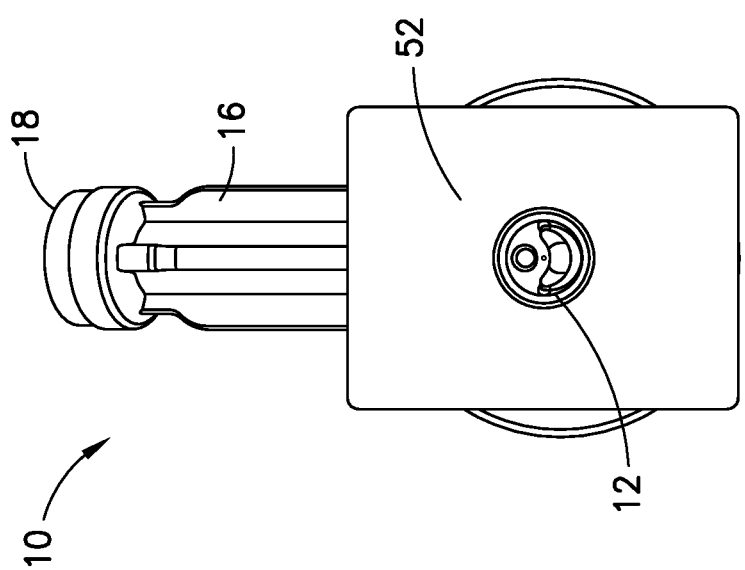
FIG. 5 is a front view of the infusion adapter of FIG. 1 according to one aspect of the present invention.

Referring to FIG. 4, in one embodiment, infusion adapter 10 may include an intravenous line connector 34 that is removably connectable to a main body 36 of infusion adapter 10. In such an embodiment, main body 36 includes an intravenous line connector receiving end 38 having a first connection portion 40. Additionally, intravenous line connector 34 includes a main body receiving end 42 having a second connection portion 44. Intravenous line connector 34 includes an end cap 46 that is pivotable via a hinge portion 48 between an open position and a closed position.

Intravenous line connector 34 may be connected to main body 36 by positioning main body receiving end 42 of intravenous line connector 34 into engagement with intravenous line connector receiving end 38 of main body 36. In one embodiment, intravenous line connector 34 may be secured to main body 36 by positioning second connection portion 44 of intravenous line connector 34 into engagement with first connection portion 40 of main body 36, and threadingly engaging first connection portion 40 and second connection portion 44. In other embodiments, second connection portion 44 of intravenous line connector 34 may be secured to first connection portion 40 of main body 36 using a press-fit, locking tapers, interference fit, snap-fit, ball detent, locking tabs, spring loaded locking mechanism, latch, adhesive, or other similar mechanism. In this manner, intravenous line connector 34 is locked to main body 36, i.e., significant relative movement between intravenous line connector 34 and main body 36 is prevented. In alternate embodiments, intravenous line connector 34 and main body 36 may be integrally formed.

Figure 7:
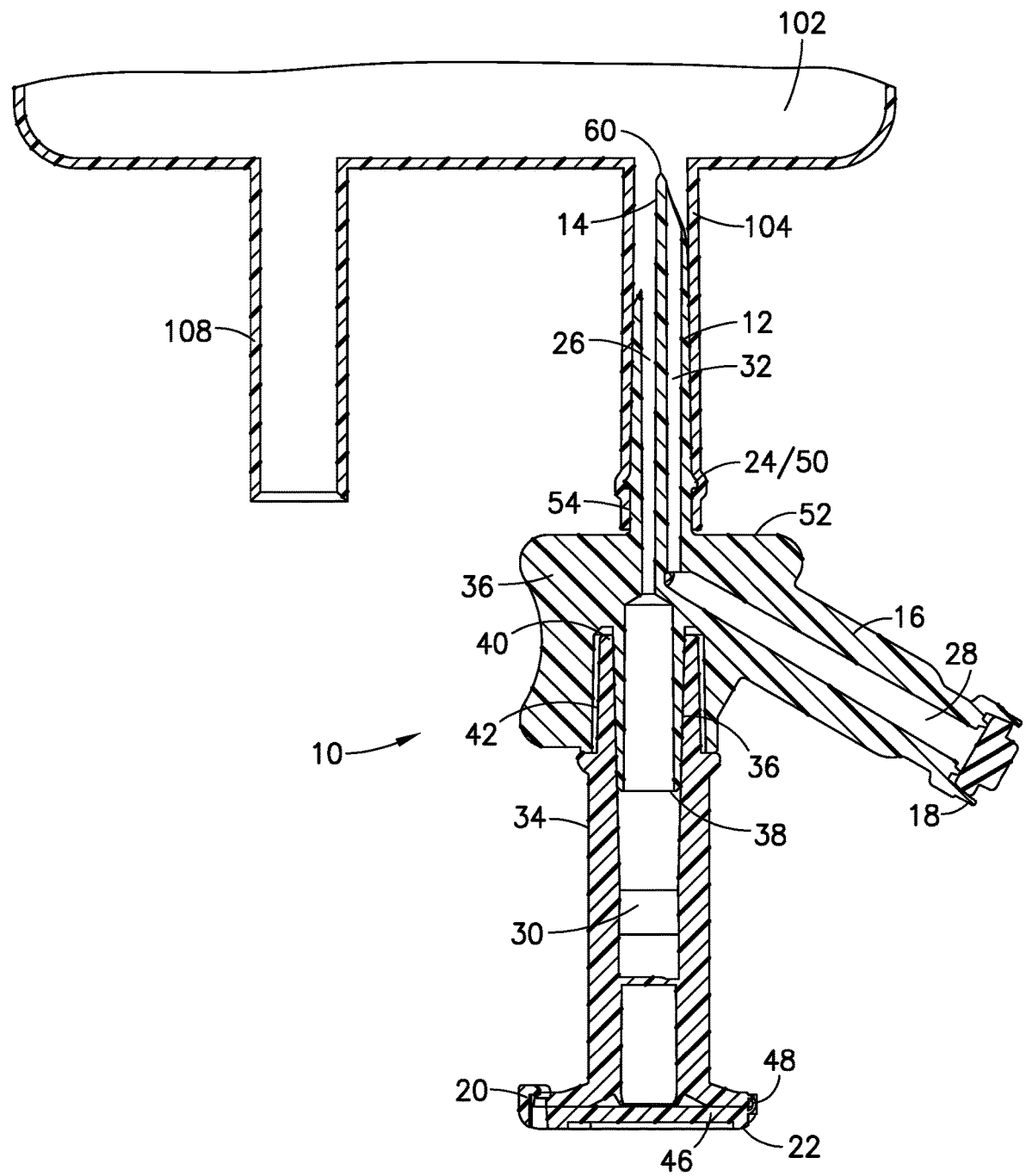
FIG. 7 is a cross-sectional view along line 4-4 shown in FIG. 3, showing the infusion adapter inserted into a port of an infusion fluid container according to one aspect of the present invention.

Referring to FIGS. 1-7, connection portion 12 of infusion adapter 10 includes anchor component 24 and a puncturing point 60 disposed adjacent first end 14. In one embodiment, anchor component 24 includes a retaining ring 50. The retaining ring 50 extends radially outward from the connection portion 12 and is positioned adjacent to a stop 52 defined by the main body 36 of the infusion adapter 10. A space 54 is provided between the retaining ring 50 and the stop 52. The retaining ring 50 has a first side 56 with a surface that is tapered and rounded and configured to ease insertion of the connection portion 12 and retaining ring 50 into an injection port of an infusion fluid container, such as an intravenous bag, which is shown in FIG. 7, and discussed in more detail below. A second side 58 of retaining ring 50 positioned opposite the first side 56 has a sharp edge 62 to resist pull out or withdrawal of the connection portion 12 from the infusion fluid container once inserted therein. A planar surface of the retaining ring 50 and the outer radial surface of the retaining ring 50 define the sharp edge 62. The retaining ring 50 is configured to provide additional retention of the infusion adapter 10 with the port of an infusion fluid container without comprising the leak-proof seal between the adapter 10 and the bag. In particular, the retaining ring 50 provides a wedging action with the port of the infusion fluid container to further secure the connection portion 12 to the bag while the relatively small profile of the retaining ring 50 maintains the leak-proof seal.

Referring to FIG. 7, the connection portion 12 of the infusion adapter 10 is inserted into the port of the infusion fluid container. Upon insertion, the compliant port of the container engages the connection portion 12 and the retaining ring 50 with the first side 56 of the retaining ring 50 allowing insertion while creating a wedging effect with the port. With the anchor component 24 of connection portion 12 connected to injection port 104 of the infusion fluid container 102, the anchor component 24 securely connects infusion adapter 10 to the infusion fluid container 102 such that disconnection of infusion adapter 10 from the infusion fluid container 102 is prevented. In this manner, anchor component 24 prevents inadvertent and accidental removal of infusion adapter 10 from infusion fluid container 102 and provides a leak-proof connection between infusion adapter 10 and infusion fluid container 102 during a drug transfer procedure. Infusion fluid container 102 may also include a second port 108.

In one embodiment, infusion adapter 10 comprises a PhaSeal adapter which is compatible with a Becton Dickinson ("BD") PhaSeal™ System available from Becton, Dickinson and Company of Franklin Lakes, N.J.

As previously discussed, intravenous therapy applications allow patients to receive infusion and medication treatment. For example, therapy may include the administration of medications by IV using intravenous and subcutaneous or hypodermis routes, i.e., into the bloodstream and under the skin. Examples of medical treatments that intravenous therapy applications may provide to a patient include antibiotics, pain management medications, cancer treatments, and similar medications.

With infusion adapter 10 securely connected to injection port 104 of infusion fluid container 102 via anchor component 24, a patient or a medical practitioner is able to connect a syringe assembly (not shown) to first port 16 of infusion adapter 10. The first port 16 may be compatible with any suitable connection arrangement and any suitable syringe adapter. With the syringe assembly connected to first port 16, a medication fluid contained in the syringe assembly can be injected into the infusion fluid container 102 via infusion adapter 10. The syringe assembly may then be disconnected from infusion adapter 10 and the infusion fluid container 102 may then be sent to nursing and is ready to be administered to a patient. For example, an intravenous line or intravenous tubing may be connected to second port 20 of infusion adapter 10 with the other end of the intravenous tubing connected to a bloodstream of a patient. In this manner, a medication may be administered to the patient intravenously.

Figure 8:
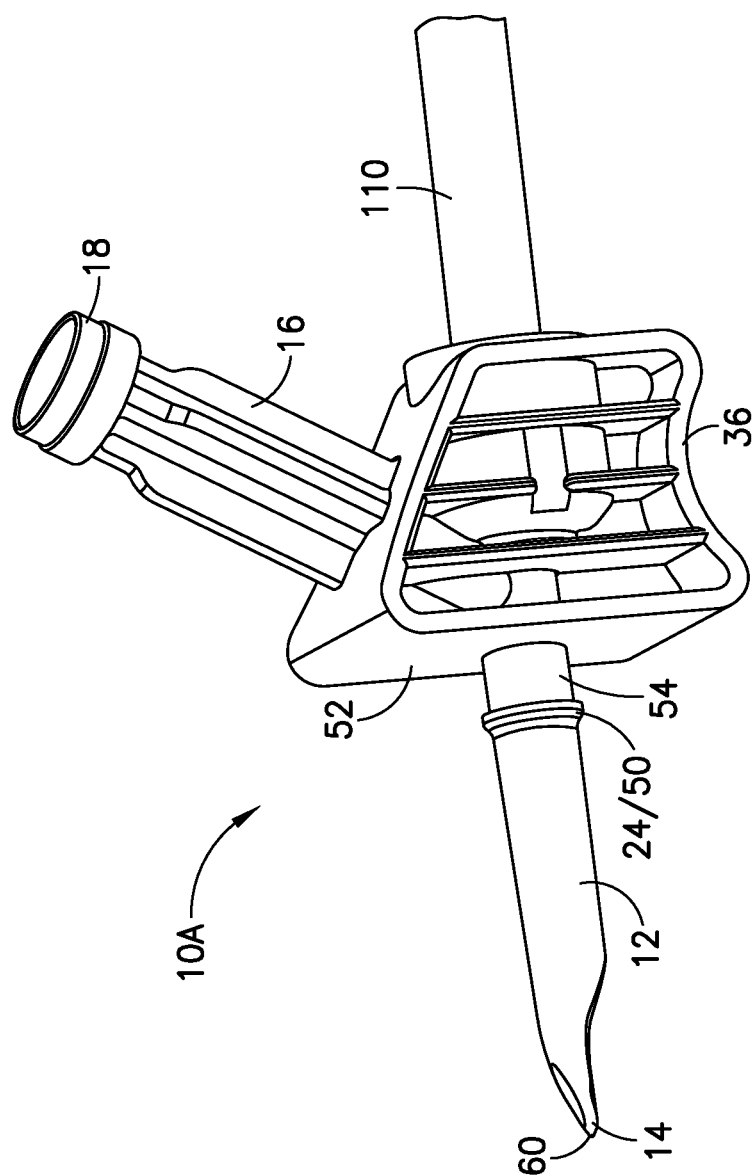
FIG. 8 is a perspective view of an infusion adapter according to a second aspect of the present invention.

Referring to FIG. 8, an infusion adapter 10A, according to a second aspect, includes a direct connection with intravenous tubing 110 rather than providing the intravenous line connector 34 shown in FIGS. 1-7.

Figure 9:
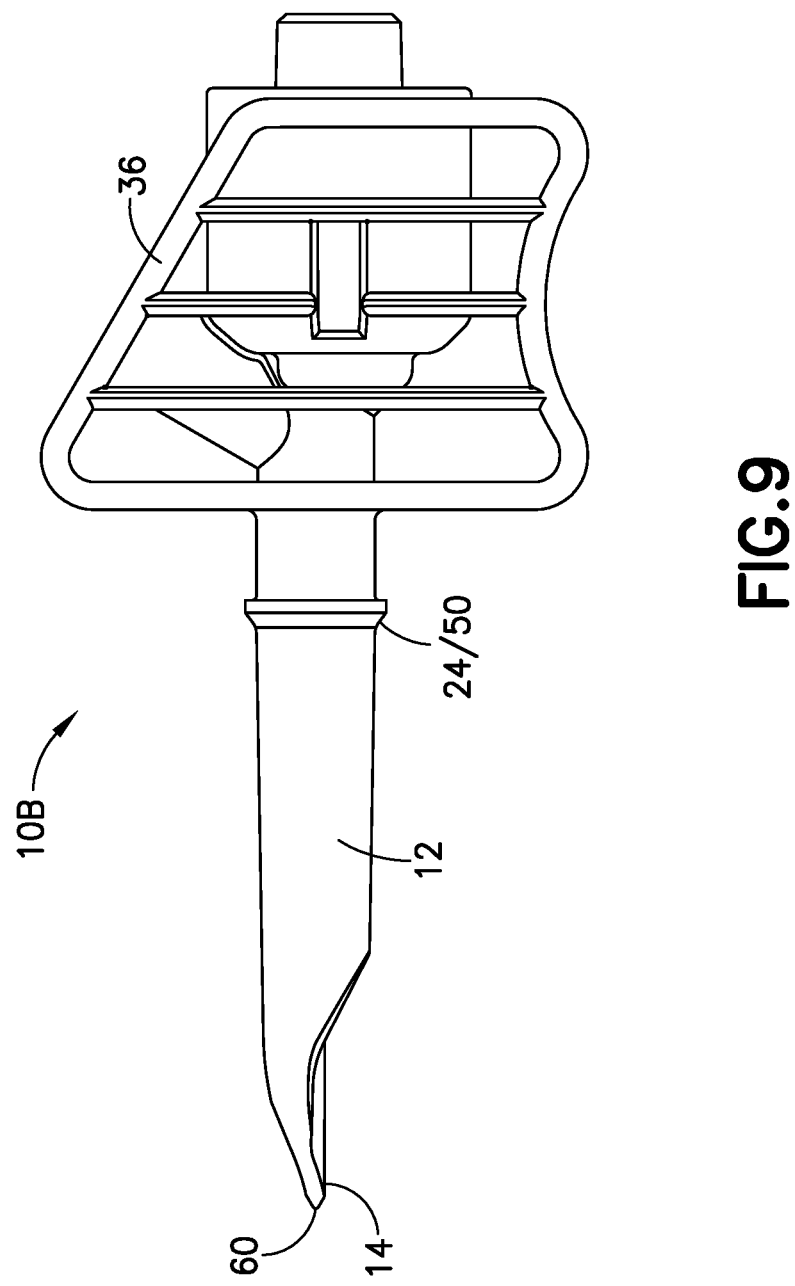
FIG. 9 is a right side view of an infusion adapter according to a third aspect of the present invention.

Referring to FIG. 9, an infusion adapter 10B, according to a third aspect, includes a direct connection for intravenous tubing and does not include the first port 16 shown in FIGS. 1-7.

Figure 10:
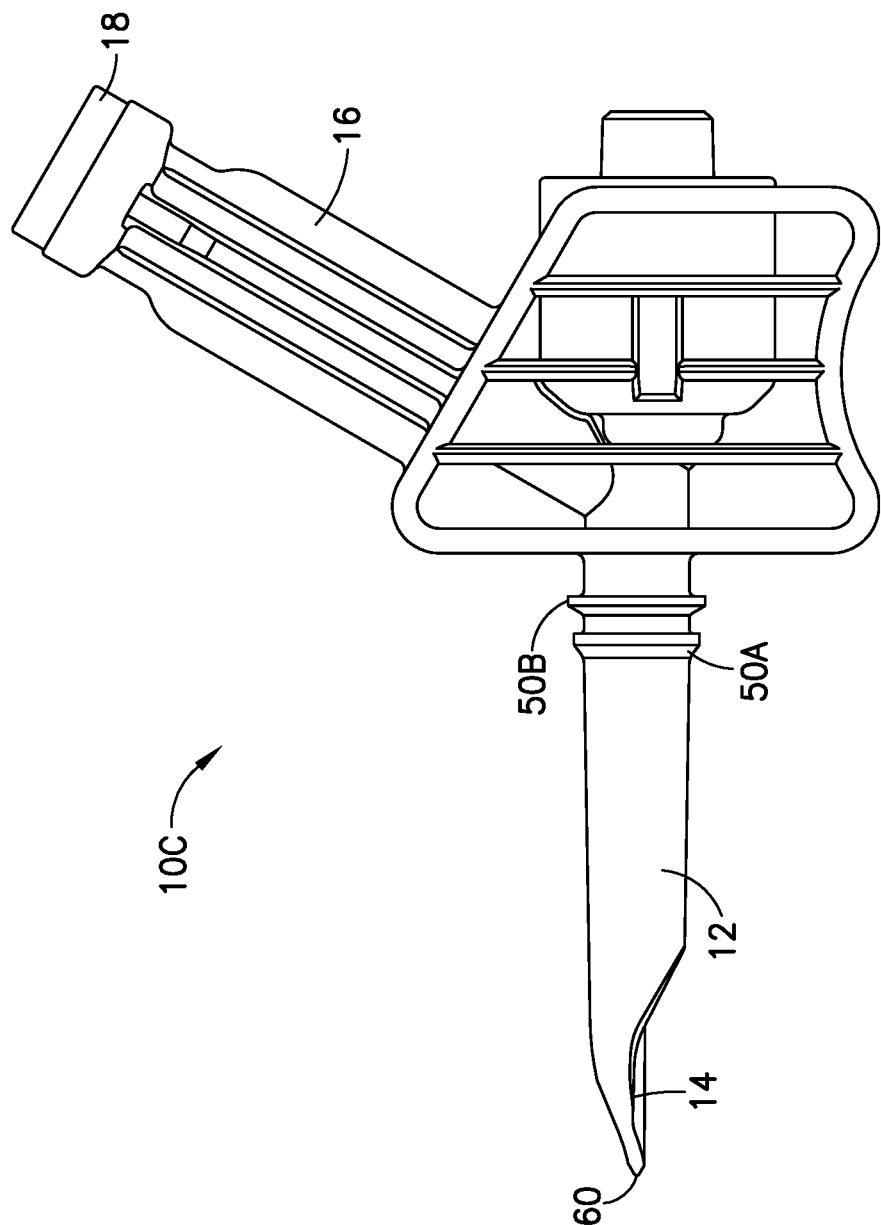
FIG. 10 is a right side view of an infusion adapter according to a fourth aspect of the present invention.

Referring to FIG. 10, an infusion adapter 10C, according to a fourth aspect, includes a plurality of retaining rings 50A, 50B. One of the retaining rings 50A, 50B may extend further radially outward than one of the other retaining rings 50A, 50B. The retaining rings 50A, 50B are spaced apart from each other along a longitudinal direction of the adapter 10C. The retaining ring 50A closest to the puncturing point 60 has a smaller diameter and extends less radially outward than the other retaining ring 50B, although other suitable configurations may be utilized.

Figure 11:
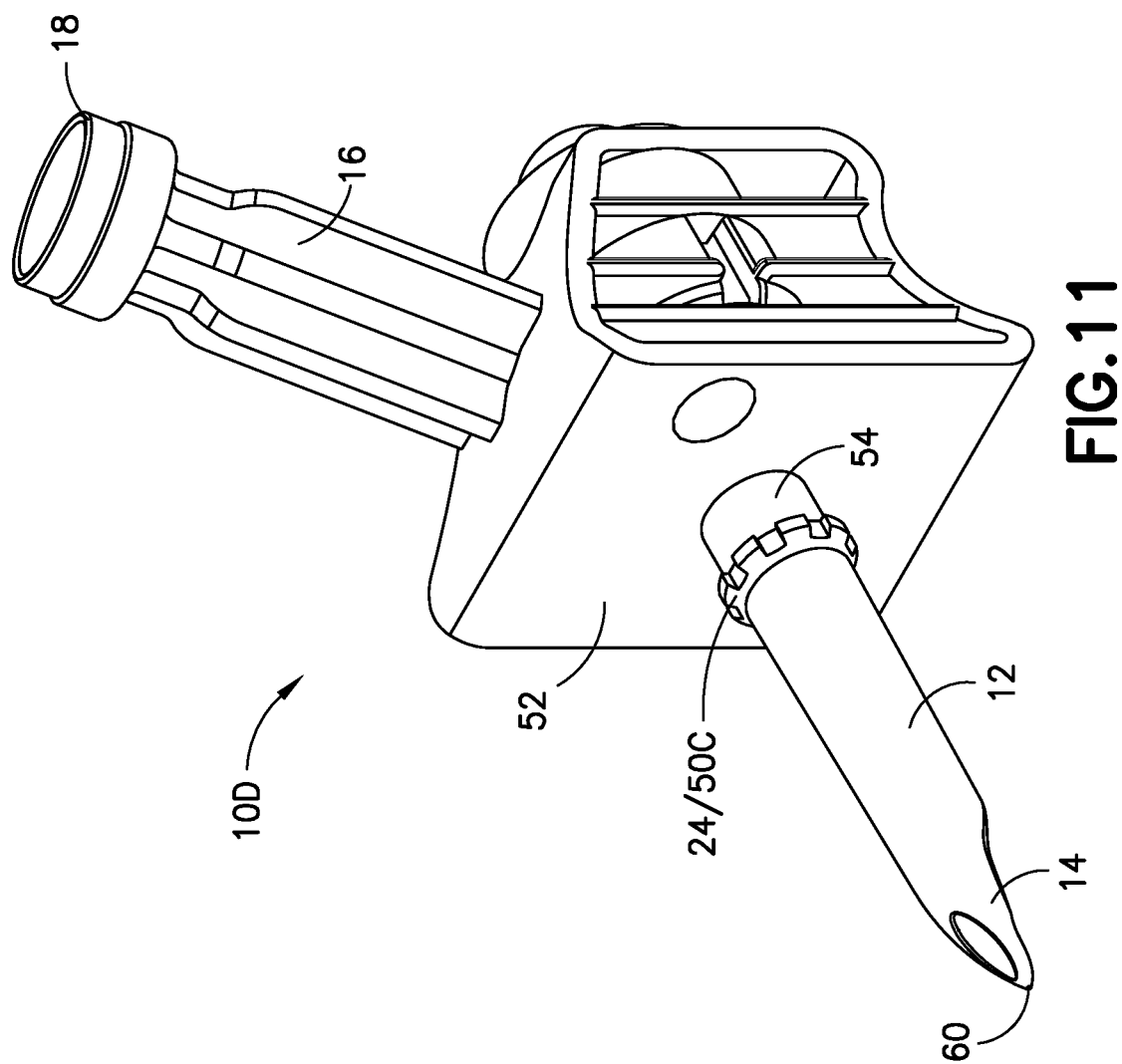
FIG. 11 is a perspective view of an infusion adapter according to a fifth aspect of the present invention.
Figure 12A:
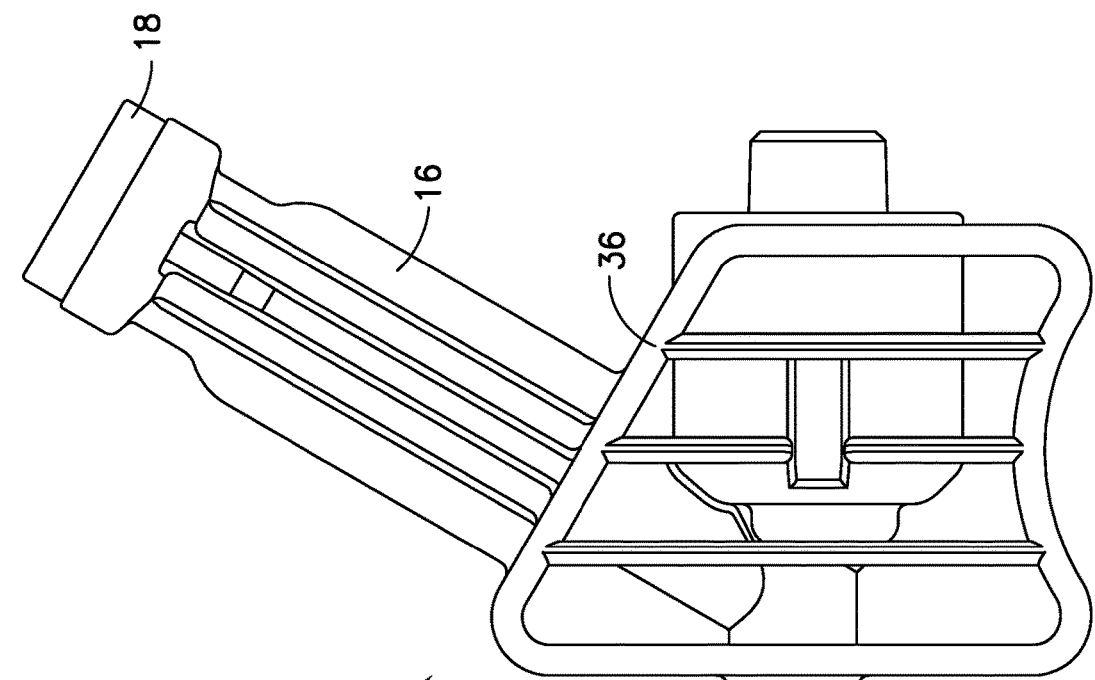
FIG. 12A is an enlarged view of area "12A" shown in FIG. 12 according to an aspect of the present invention.
Figure 12A:
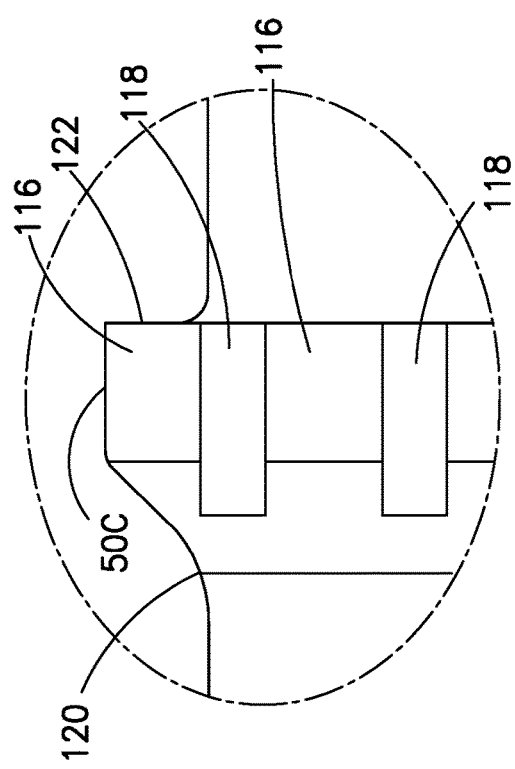
Figure 12:
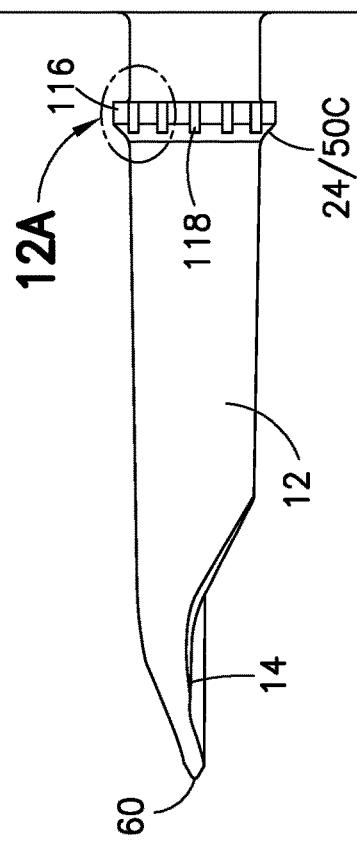
FIG. 12 is a right side view of the infusion adapter of FIG. 11 according to an aspect of the present invention.

Referring to FIGS. 11-12A, an infusion adapter 10D, according to a fifth aspect, includes a retaining ring 50C at least partially defined by a plurality of spaced apart teeth 116. The teeth 116 are defined and spaced from each other via recesses 118. The spaced apart teeth 116 and recesses 118 may be rectangular in shape. Accordingly, the retaining ring 50C of FIGS. 11-12A is crenelated. The retaining ring 50C includes a first end 120 positioned closest to the puncturing point 60 and a second end 122 positioned opposite the first end 120. The recesses 118 extend from the second end 122 to a position intermediate the first end 120 and the second end 122. The retaining ring 50C may function in a similar manner as the retaining ring 50 discussed above in connection with FIGS. 1-7 with the spaced apart teeth 116 providing additional engagement with injection port 104 of infusion fluid container 102.

Figure 13:
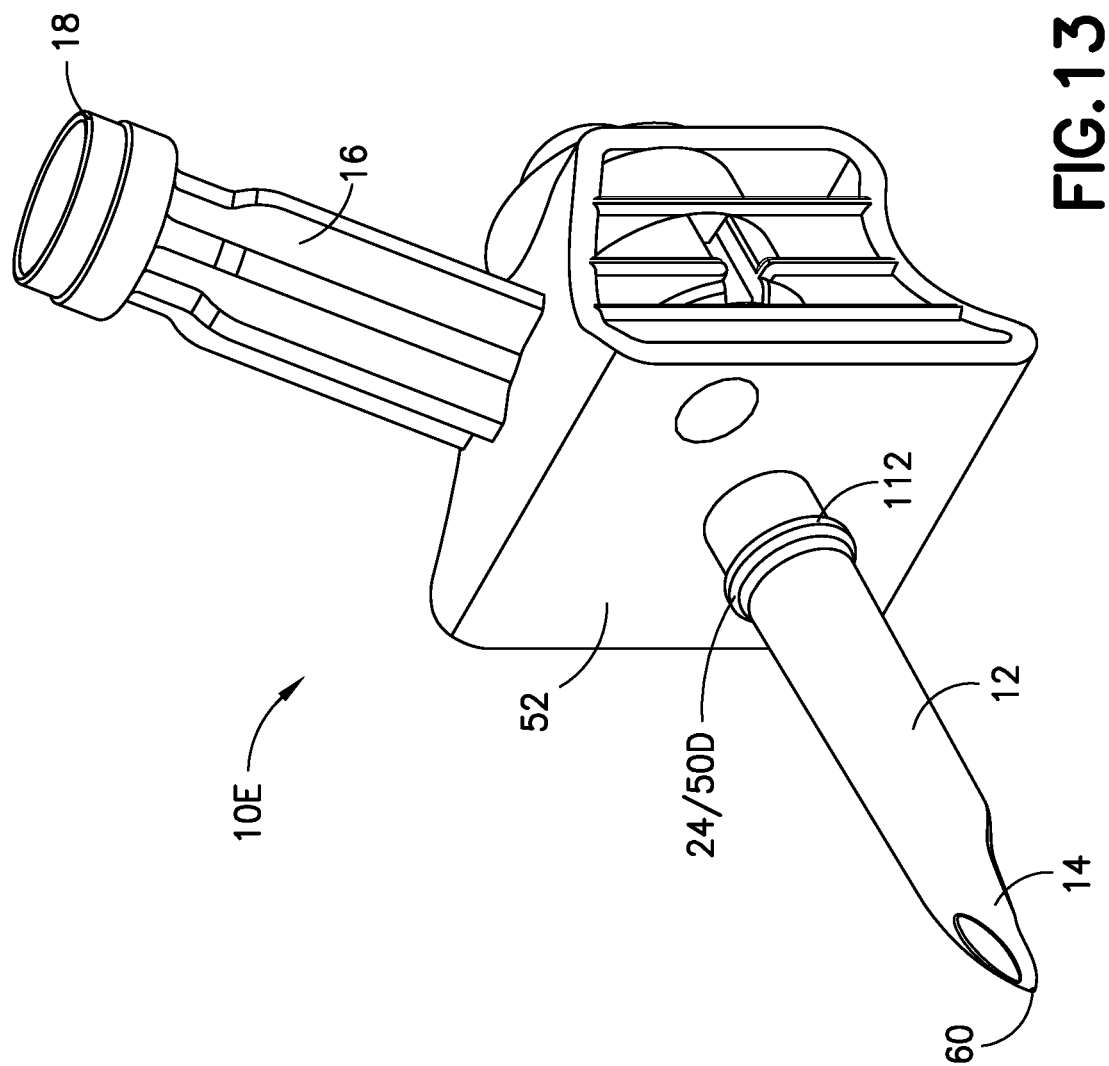
FIG. 13 is a perspective view of an infusion adapter according to a sixth aspect of the present invention.

Referring to FIG. 13, an infusion adapter 10E, according to a sixth aspect, includes a retaining ring 50D having an indicator 112, such as a colored ring-shaped area. The indicator 112 aids in visualizing the full insertion of the connection portion 12 into the injection port 104 of the infusion fluid container 102. Other suitable visual, tactile, audible, or other types of indications may be utilized.

Figures 14, 14A:
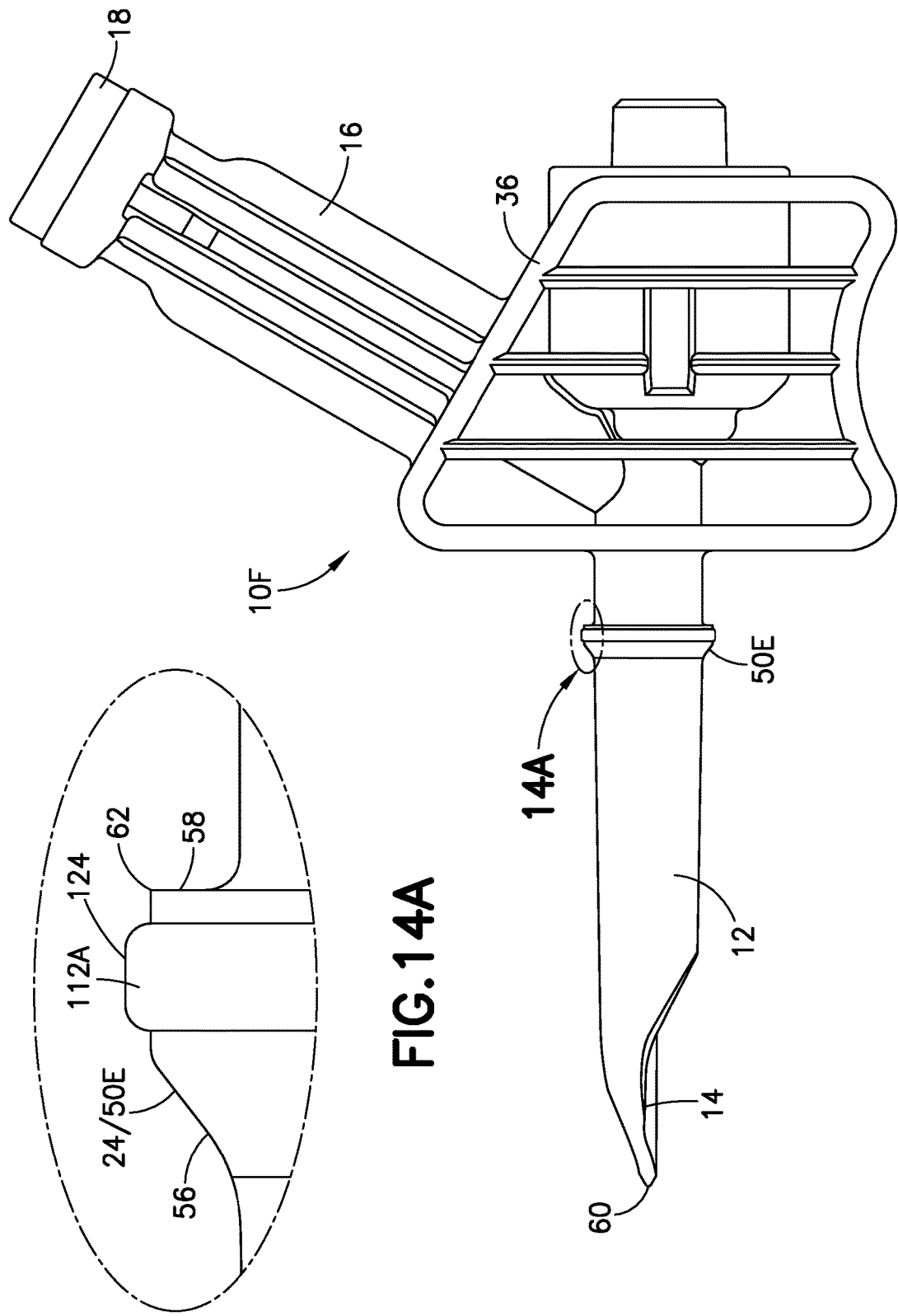
FIG. 14 is a right side view of an infusion adapter according to a seventh aspect of the present invention.
FIG. 14A is an enlarged view of area "14A" shown in FIG. 14 according to an aspect of the present invention.

Referring to FIGS. 14 and 14A, an infusion adapter 10F, according to a seventh aspect, includes a retaining ring 50E having an indicator 112A that is formed by a two-shot molding process out of an elastomeric material, such as a thermoplastic elastomer (TPE). The elastomeric material of the indicator 112A further increases the pull-out resistance of the infusion adapter 1OF from the infusion fluid container 102 by providing a higher coefficient of friction. The indicator 112A is also configured to provide visualization of insertion of the connection portion 12 into the injection port 104 of the infusion fluid container 102. In particular, inserting the connection portion 12 into the injection port 104 of the infusion fluid container 102 such that the indicator 112A is received within the injection port 104 and no longer visible outside the injection port 104 provides an indication to a user that the connection portion has been fully inserted into the injection port 104.

The retaining ring 50E, not including the indicator 112A, may be made from thermosetting polymers or thermoplastic polymers such as polypropylene, polyethylene, polystyrene, polycarbonate, acrylics, nylons, or similar materials. The indicator 112A may be annular in shape and positioned between the first side 56b and the second side 58 of the retaining ring 50E. The indicator 112A extends further radially outward than the remaining portion of the retaining ring 50E. An outer portion 124 of the indicator 112A is rounded. As noted above, the indicator 112A may be made from a material that is softer than the material of the remaining portion of the retaining ring 50E. In particular, the indicator 112A may be made from a material having a Shore A hardness between about 10-100 with the remaining portion of the retaining ring 50E being made from a material having a Shore D hardness between about 40-100.

Figure 15:
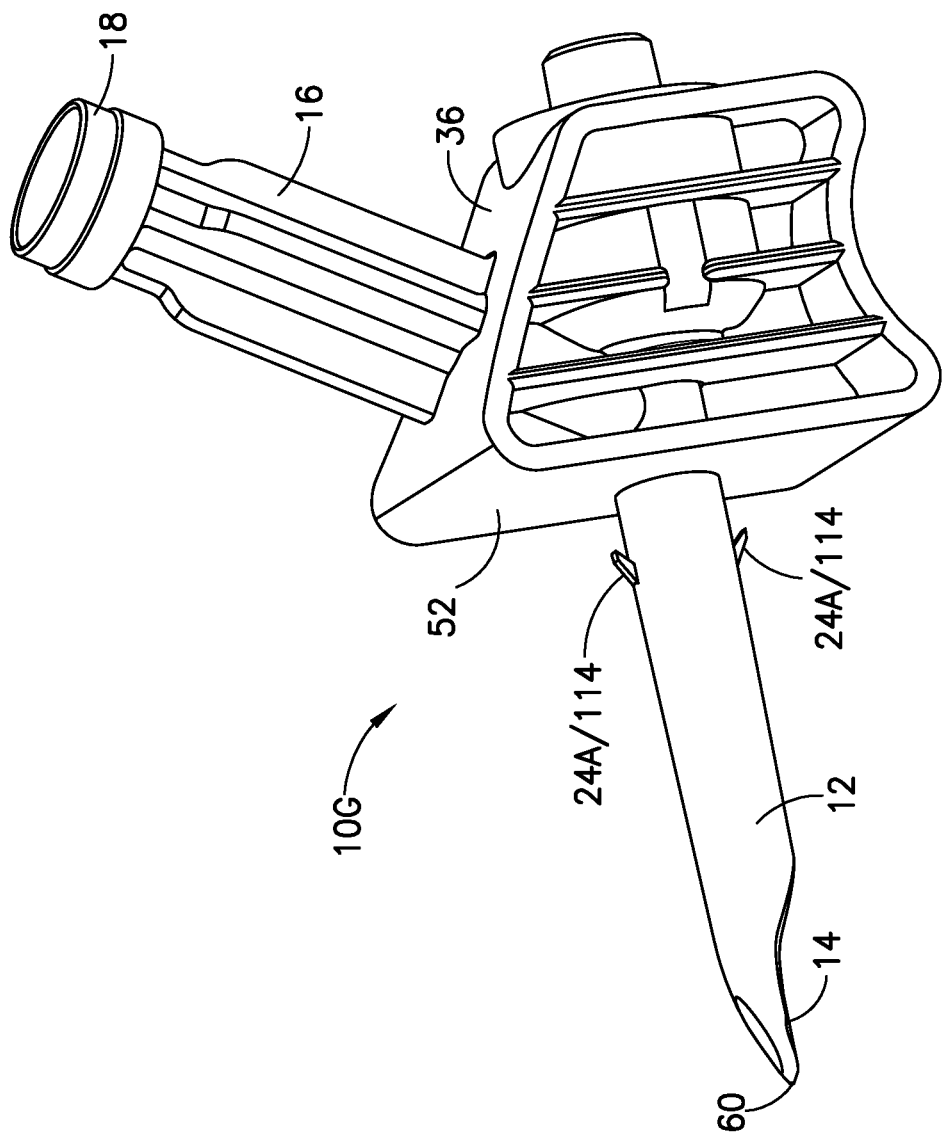
FIG. 15 is a perspective view of an infusion adapter according to an eighth aspect of the present invention.

Referring to FIG. 15, an infusion adapter 10G, according to an eighth aspect, includes an anchor component 24A that includes a plurality of barbs 114 that extend radially outward from the connection portion 12. The plurality of barbs 114 may be molded along with the rest of the connection portion 12. Each of the plurality of barbs 114 extend away from the first end 14 of the infusion adapter 10 to allow insertion of the connection portion 12 into the injection port 104 of the infusion fluid container 102, but prohibiting removing of the connection portion 12 from the injection portion 104 after insertions.

Although an indicator arrangement is shown in connection with the infusion adapters 10E, 10F, each of the other infusion adapters 10, 10A, 10B, 10C, 10D, 10G may also include an indicator that is configured to provide visualization of the insertion of the connection portion 12 into the injection port 104 of the infusion fluid container 102. The indicator may be a portion of the connection portion 12 having a different color or material than a remaining portion of the connection portion 12, although other suitable visual, tactile, audible, or other types of indications may be utilized.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An infusion adapter for connection with an infusion fluid container, the infusion adapter comprising:
   a connection portion having a length, the connection portion being configured to engage an injection port of an infusion fluid container along the entirety of the length; and
   a port configured to connect to an intravenous line, the port in fluid communication with the connection portion,
   wherein the connection portion includes a retaining ring comprising a first side and a second side positioned opposite the first side, the retaining ring extending radially outward from the connection portion, the retaining ring configured to be received within the injection port of the infusion fluid container and securely connect the infusion adapter to the infusion fluid container to substantially prevent disconnection of the infusion adapter from the infusion fluid container once the infusion adapter is connected to the infusion fluid container,
   wherein the retaining ring includes an indicator configured to provide visualization of insertion of the connection portion into an injection port of an infusion fluid container, the indicator having a different color and a different material than a remaining portion of the connection portion,
   wherein the first side of the retaining ring includes a tapered, rounded surface, and
   wherein the second side of the retaining ring defines a sharp edge that is configured to engage a portion of the infusion fluid container to restrain the infusion adapter with the infusion fluid container upon an attempt to withdraw the infusion adapter from the infusion fluid container.

2. The infusion adapter of claim 1, wherein the indicator is formed from a first material and a remaining portion of the retaining ring is formed from a second material, and wherein the first material is softer than the second material.

3. The infusion adapter of claim 1, wherein the indicator extends further radially outward than a remaining portion of the retaining ring.

4. The infusion adapter of claim 1, wherein the retaining ring is positioned adjacent to a stop defined by a main body of the infusion adapter.

5. The infusion adapter of claim 1, wherein the connection portion comprises a puncturing point.

6. The infusion adapter of claim 1, wherein the indicator is formed via a two-shot molding process.

7. The infusion adapter of claim 2, wherein the first material is an elastomeric material.

8. The infusion adapter of claim 7, wherein the first material is a thermoplastic elastomer.

9. The infusion adapter of claim 3, wherein the retaining ring includes a first side and a second side positioned opposite the first side, and wherein the indicator is annular and positioned between the first side and the second side of the retaining ring.

10. The infusion adapter of claim 3, wherein the indicator includes a rounded outer portion.

* * * * *